(12) United States Patent
Pan (10) Patent No.: US 10,779,836 B2
(45) Date of Patent: Sep. 22, 2020

(54) REPLACEABLE LEFT ATRIAL APPENDAGE OCCLUDER AND AN IMPLANTING METHOD THEREOF

(71) Applicant: Fuwai Hospital, Chinese Academy of Medical Sciences and Peking Union Medical College, Beijing., Beijing (CN)

(72) Inventor: Xiangbin Pan, Beijing (CN)

(*) Notice: Subject to any disclaimer, the term of this patent is extended or adjusted under 35 U.S.C. 154(b) by 0 days.

(21) Appl. No.: 16/648,673

(22) PCT Filed: Sep. 25, 2018

(86) PCT No.: PCT/CN2018/107185
§ 371 (c)(1),
(2) Date: Mar. 19, 2020

(87) PCT Pub. No.: WO2019/057184
PCT Pub. Date: Mar. 28, 2019

(65) Prior Publication Data
US 2020/0253613 A1    Aug. 13, 2020

(30) Foreign Application Priority Data
Sep. 25, 2017 (CN) .......................... 2017 1 0878046

(51) Int. Cl.
*A61M 29/00* (2006.01)
*A61B 17/12* (2006.01)

(52) U.S. Cl.
CPC .. *A61B 17/12122* (2013.01); *A61B 17/12031* (2013.01); *A61B 17/12136* (2013.01);
(Continued)

(58) Field of Classification Search
CPC .. A61M 29/00; A61B 17/12; A61B 17/12145; A61B 17/122; A61B 17/12036;
(Continued)

(56) References Cited

U.S. PATENT DOCUMENTS

| 6,689,150 | B1* | 2/2004 | VanTassel | A61B 17/12136 606/200 |
| 2006/0122646 | A1* | 6/2006 | Corcoran | A61B 17/0057 606/213 |
| 2015/0250482 | A1 | 9/2015 | Slaughter et al. | |

FOREIGN PATENT DOCUMENTS

| CN | 201768049 U | 3/2011 |
| CN | 103845096 A | 6/2014 |

(Continued)

*Primary Examiner* — Vi X Nguyen (57) ABSTRACT

A replaceable left atrial appendage occluder includes a stepped balloon and an occlusion disc. The left atrial appendage orifice occlusion portion of the stepped balloon is configured to completely occlude the left atrial appendage orifice. The left atrial anchor portion of the stepped balloon is configured to be clamped on the left atrial wall to prevent the left atrial appendage occluder from shifting. The occlusion disc is released in the pericardial cavity, and is connected to the stepped balloon by the connecting column of the occlusion disc, so that the left atrial appendage is pressed and occluded between the stepped balloon and the occlusion disc. The stepped balloon occludes the left atrial appendage orifice. The surface of the stepped balloon is smooth and coated with an anticoagulant coating.

10 Claims, 6 Drawing Sheets

(52) U.S. Cl.
CPC .. *A61B 17/12177* (2013.01); *A61B 17/12186* (2013.01); *A61B 2017/1205* (2013.01)

(58) Field of Classification Search
CPC ...... A61B 17/12172; A61B 2017/1205; A61B 17/12022
See application file for complete search history.

(56) References Cited

FOREIGN PATENT DOCUMENTS

| | | |
|---|---|---|
| CN | 104274224 A | 1/2015 |
| CN | 104306040 A | 1/2015 |
| CN | 106344100 A | 1/2017 |
| CN | 106859722 A | 6/2017 |
| CN | 107595347 A | 1/2018 |

* cited by examiner

REPLACEABLE LEFT ATRIAL APPENDAGE OCCLUDER AND AN IMPLANTING METHOD THEREOF

CROSS REFERENCE TO THE RELATED APPLICATIONS

This application is the national phase entry of International Application No. PCT/CN2018/107185, filed on Sep. 25, 2018, which is based upon and claims priority to Chinese Patent Application No. 201710878046.7, filed on Sep. 25, 2017, the entire contents of which are incorporated herein by reference.

TECHNICAL FIELD

The present disclosure belongs to the field of biomedical instruments, and specifically relates to a replaceable left atrial appendage occluder and an implanting method thereof.

BACKGROUND

In the left atrial appendage occlusion, the occlusion device is placed in a delivery sheath and is delivered to the left atrial appendage orifice by a minimally invasive puncture of the atrial septum, so as to occlude the left atrial appendage and isolate the left atrium from the left atrial appendage, which prevents blood clots generated in the left atrial appendage from entering the bloodstream, and avoids the stroke caused by atrial fibrillation.

Figure 1:
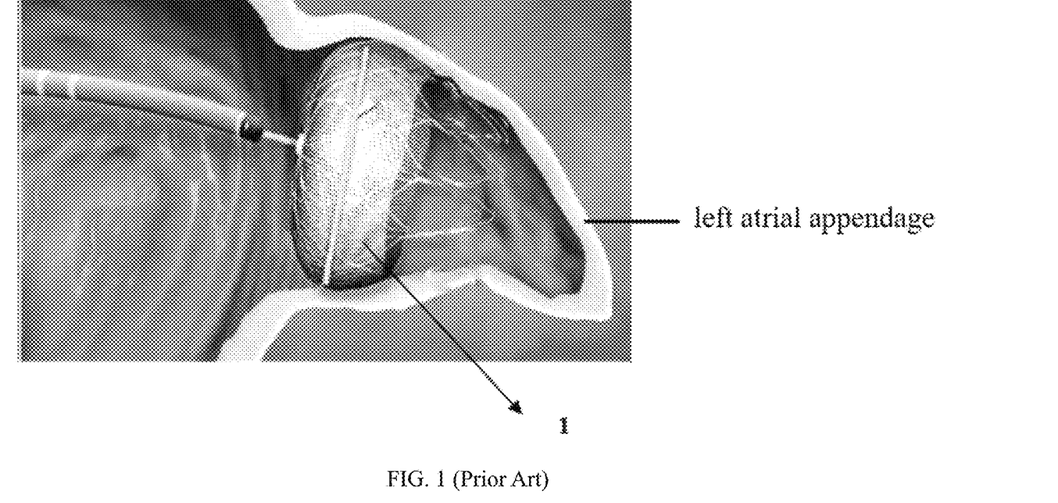
FIG. 1 is a structural schematic diagram of the left atrial appendage occlusion device in the prior art.

In general, in the prior art, the occlusion umbrella is delivered to the left atrial appendage orifice to completely seal the left atrial appendage orifice, and an occlusion disc is arranged behind the occlusion umbrella to support the left atrial appendage wall, so as to fix the whole occlusion device. For example, in the prior art, the Chinese invention patent No. 201610885243.7, titled Left Atrial Appendage Occlusion Device, and the Chinese invention patent No. 201410528043.7, titled Left Atrial Appendage Occlusion Device, both recorded that outer surfaces of the occlusion device need to be provided with barbs, and the umbrella-shaped plate is made of a metal mesh. FIG. 1 is a schematic diagram showing the structure of the occlusion device in the prior art, which has the following deficiencies. 1. This structure has strict demands on the shape of the atrial appendage. However, a number of patients have an irregular lobulation of the atrial appendage or have the atrial appendage with an insufficient depth, leading to an occlusion failure or incomplete occlusion. 2. Existing occlusion devices are provided with barbs to prevent the occlusion device from displacement. After the occlusion device is released, the barbs are inserted into the left atrial wall to stabilize the occlusion device. However, the barbs are inserted with an uncontrollable depth and direction, and thus are more likely to penetrate the atrial wall and cause the pericardial effusion. 3. Existing occlusion devices use a large area of nickel-titanium alloy framework to contact the bloodstream. In order to avoid the thrombus formation, patients must take a large number of anticoagulant drugs for six months after the procedure, but patients who need the treatment of left atrial appendage occlusion often have a contraindication to anticoagulant drugs or have a poor anticoagulant effect.

Therefore, it is imperative to develop a novel left atrial appendage occlusion device capable of reducing the use of the metal mesh used in the occlusion device, reducing the chance of thrombosis after the procedure, and adapting to left atrial appendage orifices with different morphologies, which improves the applicability of the occlusion device.

SUMMARY

In order to overcome the above-mentioned issues, in the present disclosure, the left atrial appendage occlusion device consists of a balloon and an occlusion disc respectively arranged on the left side and the right side of the device. This device is implanted by penetrating the left atrial appendage. The balloon and the occlusion disc are connected and fixed to each other, and arranged on the left side and the right side of the left atrial appendage, respectively. The balloon and the occlusion disc of the present disclosure are replaceable and detachable, which increases the flexibility of the left atrial appendage occlusion device.

The technical solutions of the present disclosure are as follows:

A replaceable left atrial appendage occluder includes a stepped balloon and an occlusion disc, wherein, the stepped balloon and the occlusion disc are connected and fixed to each other, and arranged on the left side and the right side of a left atrial appendage, respectively, so that the left atrial appendage is pressed and occluded between the stepped balloon and the occlusion disc.

The occlusion disc is an elastic umbrella-shaped mesh structure, and a barrier patch is arranged inside the occlusion disc.

The stepped balloon is a hollow structure. The stepped balloon after being filled forms a left atrial appendage orifice occlusion portion and a left atrial anchor portion. The diameter of the left atrial appendage orifice occlusion portion is larger than the left atrial appendage orifice, and thus the left atrial appendage orifice occlusion portion is configured to completely fill and occlude the left atrial appendage orifice. The diameter of the left atrial anchor portion is larger than the diameter of the left atrial appendage orifice occlusion portion, and the left atrial anchor portion is clamped on a left atrial wall of the left atrial appendage orifice to prevent the stepped balloon from sliding into the left atrial appendage.

A balloon filling inlet is arranged at the connection between the stepped balloon and a sheath catheter, and is configured to inject a liquid into the stepped balloon. A movable cover membrane is arranged on the surface of the left atrial anchor portion. The surface of the stepped balloon is sealed after the movable cover membrane is closed.

Further, a penetrating passage is arranged in the stepped balloon, and a connecting column is arranged at the lower portion of the occlusion disc. The stepped balloon and the occlusion disc are fixed to each other by the extension connection of the penetrating passage and the connecting column.

Further, a groove is arranged on the inner wall of the penetrating passage, and an annular protrusion is arranged on the outer periphery of the connecting column. The groove is engaged with the annular protrusion when the stepped balloon is connected to the occlusion disc.

Further, a sheath catheter connection point is arranged at the left atrial end of the penetrating passage, wherein the sheath catheter connection point is a groove or a cannula.

Further, the diameter of the left atrial appendage orifice occlusion portion is 2-8 mm larger than the left atrial appendage orifice; the diameter of the left side umbrella-shaped plate of the occlusion disc is 10-50 mm, and the diameter of the connecting column is 2-20 mm.

The length of the stepped balloon is 10-60 mm, the diameter of the left atrial appendage orifice occlusion portion is 10-90 mm, the diameter of the left atrial anchor portion is 20-100 mm, the thickness of the left atrial anchor portion is 4-20 mm, and the diameter of the left atrial anchor portion is 4-30 mm larger than the diameter of the left atrial appendage orifice occlusion portion.

Further, the diameter of the left side umbrella-shaped plate of the occlusion disc is 30 mm, and the diameter of the connecting column is 8 mm.

The length of the stepped balloon is 20 mm, the diameter of the left atrial anchor portion is 10 mm larger than the diameter of the left atrial appendage orifice occlusion portion, and the thickness of the left atrial anchor portion is 6 mm. The stepped balloons have different sizes, wherein the different sizes are divided by every 5 mm of lengths and diameters, and selected according to the size of the left atrial appendage orifice.

Further, the material of the stepped balloon is a polymer, rubber, or a polyester material, and the surface of the stepped balloon is coated with an anticoagulant coating.

An implanting method for the left atrial appendage occlusion device includes the following steps:

step 1, conventionally delivering a catheter and a guide wire to the right atrium through a femoral vein; retaining the guide wire in the left atrium after puncturing the atrial septum; connecting the balloon sheath catheter to the stepped balloon by the sheath catheter connection point; inserting a dilator into the balloon sheath catheter; delivering the dilator and the balloon sheath catheter to the left atrium along the guide wire; withdrawing the dilator; delivering a pigtail catheter through the balloon sheath catheter; adjusting a direction of the catheter; delivering the pigtail catheter into the left atrial appendage; delivering the balloon sheath catheter into the left atrial appendage along the pigtail catheter; and filling the stepped balloon with a liquid through a water injection port at the distal end of the balloon sheath catheter; wherein the left atrial appendage orifice is completely occluded by the stepped balloon; the filling inlet connected to the balloon sheath catheter on the balloon is provided with a one-way valve; the balloon sheath catheter is provided with a hose; the hose is inserted into the one-way valve to inject water into and pump water from the balloon; the hose is pulled out after the left atrial appendage orifice is completely occluded; and the one-way valve on the balloon is automatically closed to prevent the liquid from leaking out;

step 2, pumping remaining blood in the left atrial appendage through the pigtail catheter, withdrawing the pigtail catheter, and inserting an occlusion device delivery sheath catheter along the balloon sheath catheter; wherein the delivery sheath catheter is provided with the dilator; inserting the guide wire along the delivery sheath catheter to penetrate the left atrial appendage into the pericardial cavity with a high-frequency electrical energy; delivering the occlusion device delivery sheath catheter along the guide wire to enter the pericardial cavity through the left atrial appendage; after exchanging a left atrial guide wire to enter the pericardial cavity, withdrawing the dilator and the guide wire and retaining the occlusion device delivery sheath catheter in the pericardial cavity;

step 3, delivering the left atrial appendage occluder along the delivery sheath catheter after the occlusion disc is connected to an occlusion disc connecting steel cable; releasing the canopy of the occlusion disc in the pericardial cavity; retracting the delivery sheath catheter; pressing the left atrial appendage between the occlusion disc and the stepped balloon; fixing the push rod and the balloon sheath catheter; continuing to retract the delivery sheath catheter; and releasing the connecting column of the occlusion disc inside the balloon sheath catheter; wherein the connecting column expands, the groove on the inner wall of the penetrating passage of the balloon is engaged with the annular protrusion on the outer periphery of the connecting column, and the occlusion disc can be released by rotating the connecting steel cable; withdrawing the occlusion disc connecting steel cable and the occlusion device delivery sheath catheter; disconnecting the balloon sheath catheter from the stepped balloon, and completely releasing the left atrial appendage occlusion device; wherein, the movable cover membrane on the stepped balloon naturally disengages after the balloon sheath catheter is withdrawn; and the sheath catheter connection point and the penetrating passage are closed.

Further, in step 3, the hose is arranged in the water injection port at the distal end of the balloon sheath catheter; the head end of the hose is inserted into the one-way valve; water is injected into or pumped from the balloon through the hose before the balloon is separated from the sheath catheter; after the occlusion is completed and inspected, the hose is retracted to the water injection port at the distal end of the balloon sheath catheter; the hose is retracted into the sheath catheter, and the balloon sheath catheter is separated from the balloon by rotating the balloon sheath catheter.

Further, before the occlusion disc is released by rotating the connecting steel cable, inspecting whether the replaceable left atrial appendage occluder successfully occludes the left atrial appendage orifice by push and pull experiments, ultrasonic testing, and an angiographic evaluation; withdrawing the replaceable left atrial appendage occluder, and increasing a pressure, or replacing the replaceable left atrial appendage occluder with a different size of the replaceable left atrial appendage occlusion device as needed.

The present disclosure has the following advantages by using the above-mentioned technical solutions:

1. The left atrial appendage occluder of the present disclosure does not need anticoagulation after the procedure. In traditional occlusion devices, a metal surface contacts the blood, which is extremely prone to produce a thrombus formation, and patients must take multiple oral anticoagulant drugs. In the present disclosure, the left atrial appendage occluder uses a stepped balloon having a smooth surface to occlude the left atrial appendage orifice, and the stepped balloon without metal materials is less likely to produce a thrombus formation. Therefore, it is unnecessary to take anticoagulant drugs after the procedure when the occlusion device of the present disclosure is used.

2. The occluder of the present disclosure is less likely to disengage. In the present disclosure, the left atrial appendage is occluded according to the clamping principle. However, traditional left atrial appendage occlusion devices insert the barbs into the myocardium to maintain the stability, which poses a risk of disengagement, and is prone to complications such as bleeding and pericardial tamponade. The left atrial appendage occlusion device of the present disclosure is not provided with barbs that are inserted into the myocardium, and two ends of the clamping structure are securely fixed, which greatly reduces the risk of disengagement of the left atrial appendage occlusion device and the risk of bleeding of the left atrium.

3. The left atrial appendage orifice can be immediately and completely occluded, which is significantly effective. Traditional left atrial appendage occlusion devices use a metal stent provided with a diaphragm to occlude the blood flow. As a result, there is inevitably a gap, which takes a long time to wait for the thrombus and endothelialization to completely occlude the blood flow. In the present disclosure, the balloon is configured to directly occlude the left atrial appendage orifice, which can immediately and completely occlude the blood flow.

4. The occlusion device of the present disclosure can adapt to left atrial appendage orifices of different sizes and shapes, and thus has a high applicability. Since traditional left atrial appendage occlusion devices need to be implanted in the left atrial appendage, the shape and the depth of the left atrial appendage are strictly required. In the present disclosure, the left atrial appendage is completely pressed according to the clamping principle without being affected by the shape of the left atrial appendage, and the occlusion device can occlude various types of left atrial appendages of patients.

5. The occlusion device of the present disclosure can be withdrawn and released repeatedly. If the systematic positioning is not satisfactory, the balloon and the occlusion disc can be completely withdrawn to occlude again. After use, the size of the occlusion device can be replaced as required, which improves the utilization rate of the occlusion device and significantly improves the occlusion effect.

where, 1—occlusion device in the prior art, 2—stepped balloon, 21—movable cover membrane, 22—penetrating passage, 23—groove, 24—balloon filling inlet, 25—sheath catheter connection point, 211—left atrial appendage orifice occlusion portion, 212—left atrial anchor portion, 3—occlusion disc, 31—connecting column, 32—annulus protrusion.

DETAILED DESCRIPTION OF THE EMBODIMENTS

In order to clearly describe the objectives, technical solutions, and advantages of the present disclosure, the present disclosure will be further described in detail hereinafter with reference to the drawings and embodiments. It should be understood that the structural diagrams and specific embodiments described herein are only intended to illustrate the present disclosure rather than limit the same.

Embodiment 1

Figure 2:
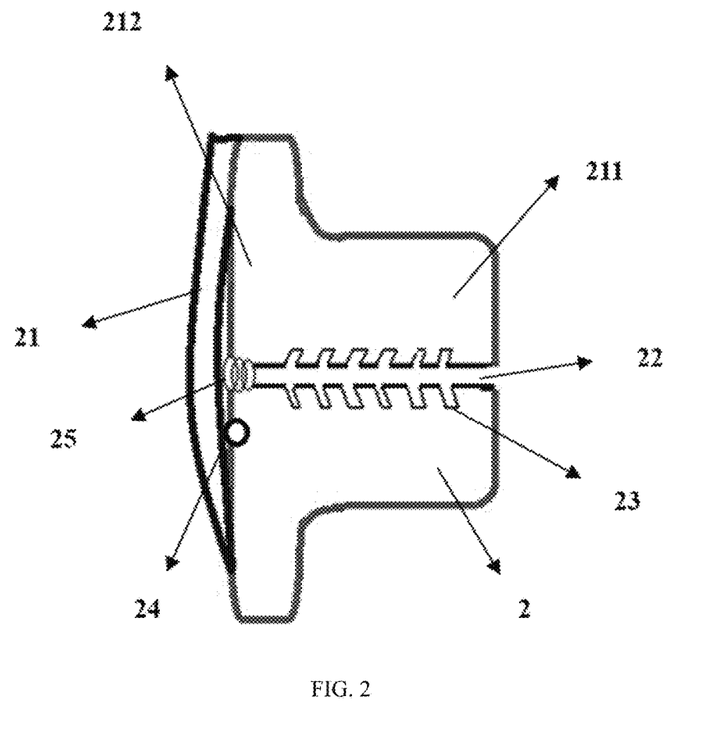
FIG. 2 is a side view showing a filled state of the stepped balloon of the left atrial appendage occluder of the present disclosure.
Figure 3:
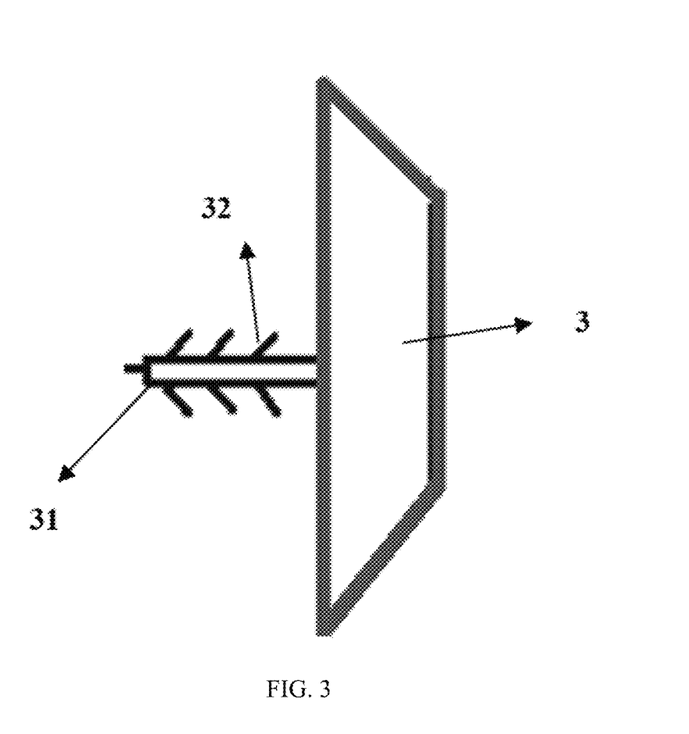
FIG. 3 is a side view showing an unfolded state of the occlusion disc of the left atrial appendage occluder of the present disclosure.
Figure 4:
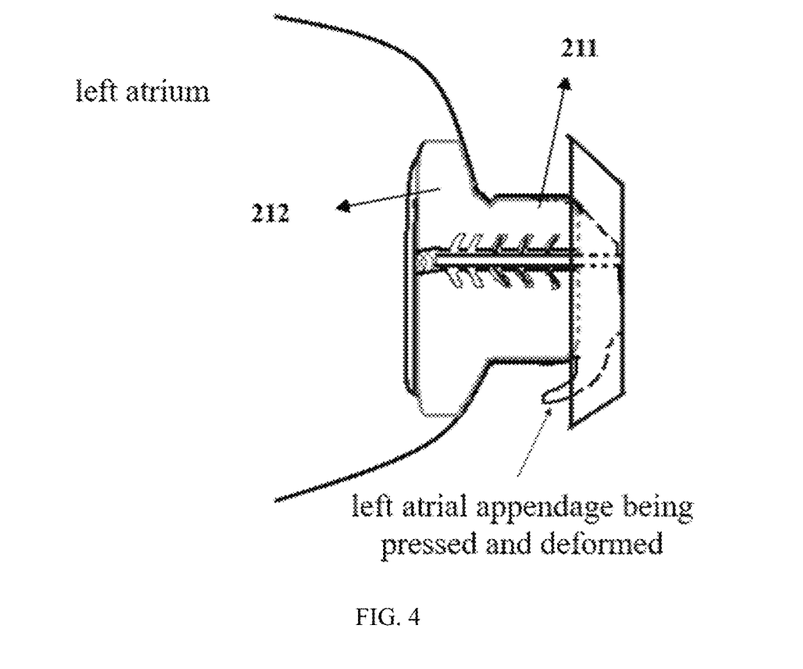
FIG. 4 is a structural schematic diagram of the left atrial appendage occluder fixed at the left atrial appendage orifice according to the present disclosure.

As shown in FIGS. 2-4, the present disclosure provides a replaceable left atrial appendage occluder, including the stepped balloon 2 and the occlusion disc 3. The stepped balloon and the occlusion disc are connected and fixed to each other, and arranged on the left side and the right side of the left atrial appendage, respectively, so as to press the left atrial appendage between the stepped balloon and the occlusion disc. The occlusion disc is an elastic umbrella-shaped mesh structure, and a barrier patch is arranged inside the occlusion disc. The overall structure of the occlusion disc can be consistent with the umbrella-shaped plate in the prior art. The occlusion disc is configured to cover the left atrial appendage on the right side of the left atrial appendage, and cooperates with the balloon to press and fix the left atrial appendage between the stepped balloon and the occlusion disc. A small area of metal structure, provided on the side of the occlusion disc that contacts the left atrial appendage, contacts the blood, and is usually made of a nickel-titanium alloy material.

The stepped balloon 2 is a hollow structure, and can shrink to reach the left atrial appendage orifice through the catheter. The surface of the stepped balloon that contacts the left atrium is provided with the balloon filling inlet 24. The balloon filling inlet is connected to the sheath catheter. The balloon is filled with a liquid from the inner surface of the threaded interface to be bulged, and the liquid is a conventional liquid for surgery, e.g. normal saline, and the like. After being filled, the stepped balloon forms the left atrial appendage orifice occlusion portion 211 and the left atrial anchor portion 212. The diameter of the left atrial appendage orifice occlusion portion is larger than the left atrial appendage orifice. Preferably, the diameter of the left atrial appendage orifice occlusion portion is 2-8 mm larger than the left atrial appendage orifice and thus the left atrial appendage orifice occlusion portion is configured to completely fill and occlude the left atrial appendage orifice. The diameter of the left atrial anchor portion is larger than the diameter of the left atrial appendage orifice occlusion portion, and the left atrial anchor portion is clamped on the left atrial wall of the left atrial appendage orifice.

The material of the stepped balloon is a polymer, e.g. rubber, polyester materials, and the like, and the surface of the stepped balloon is coated with an anticoagulant coating. The structure and material of the balloon of the present disclosure greatly reduce the formation of thrombus and anticoagulation is, therefore, not needed after the procedure. This effectively improves the safety and the quality of life of the patient.

The diameter of the left side umbrella-shaped plate of the occlusion disc 3 is 10-50 mm. The diameter of the connecting column is 2-20 mm. The length of the stepped balloon is 10-60 mm. The diameter of the left atrial appendage orifice occlusion portion is 10-90 mm. The diameter of the left atrial anchor portion is 20-100 mm. The thickness of the left atrial anchor portion is 4-20 mm. The diameter of the left atrial anchor portion is 4-30 mm larger than the diameter of the left atrial appendage orifice occlusion portion.

Preferably, the diameter of the left side umbrella-shaped plate of the occlusion disc is 30 mm, and the diameter of the right side umbrella-shaped plate of the occlusion disc is 20 mm. The diameter of the connecting column is 8 mm. The length of the stepped balloon is 20 mm. The diameter of the left atrial anchor portion is 10 mm larger than the diameter of the left atrial appendage orifice occlusion portion. The thickness of the left atrial anchor portion is 6 mm.

The stepped balloons have different sizes, which are divided by every 5 mm of lengths and diameters, and the size is selected according to the size of the left atrial appendage orifice.

A movable cover membrane is arranged on the surface of the left atrial anchor portion. The movable cover membrane can be opened upwards when the surface of the left atrial anchor portion needs to be connected to the sheath catheter or filled with the liquid. After the procedure is completed, the sheath catheter is withdrawn and the movable cover membrane automatically moves downward. The surface of the left atrial anchor portion can be occluded when the movable cover membrane is closed.

Embodiment 2

In the present disclosure, the stepped balloon and the occlusion disc can be connected and fixed in various manners. Preferably, the present embodiment provides an expandable structure for connecting and fixing.

As shown in FIG. 4, the penetrating passage 22 is arranged in the stepped balloon, and the connecting column 31 is arranged on the side of the occlusion disc 3 that contacts the left atrial appendage. The diameter of the connecting column is slightly larger than the inner diameter of the penetrating passage. The stepped balloon and the occlusion disc are fixed to each other by the extension connection of the penetrating passage and the connecting column.

As shown in FIGS. 6a-6e, preferably, the filling inlet 24 is arranged in the penetrating passage, and the water is regulated by the water stop valve and injected into the stepped balloon by the water injection hose on the balloon sheath catheter.

The groove 23 is arranged on the inner wall of the penetrating passage, and the annular protrusion 32 is arranged on the outer periphery of the connecting column. The groove is engaged with the annular protrusion when the stepped balloon is connected to the occlusion disc, which increases the consolidation of the device.

The sheath catheter connection point 25 is arranged at the left atrial end of the penetrating passage, and is configured to connect and fix the balloon sheath catheter. The sheath catheter connection point can be a groove structure connected to the groove of the balloon sheath catheter, or a cannula structure sleeved and fixed to the balloon sheath catheter. The connection method of the sheath catheter connection point is not limited by the present disclosure. Any structure capable of realizing this connection can be used.

Embodiment 3

Figure 5A:
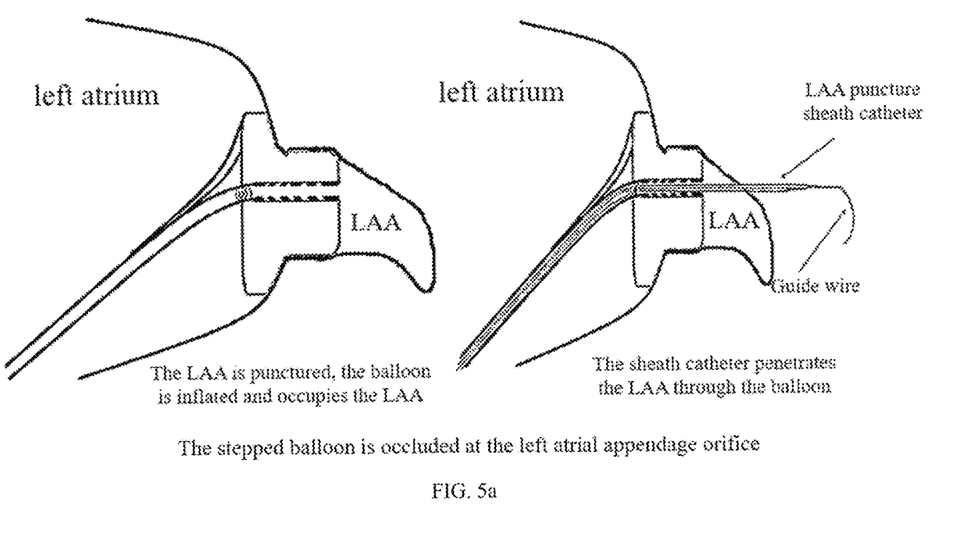
FIGS. 5*a*-5*c* show an implanting process of the left atrial appendage occluder according to the present disclosure.
Figure 5B:
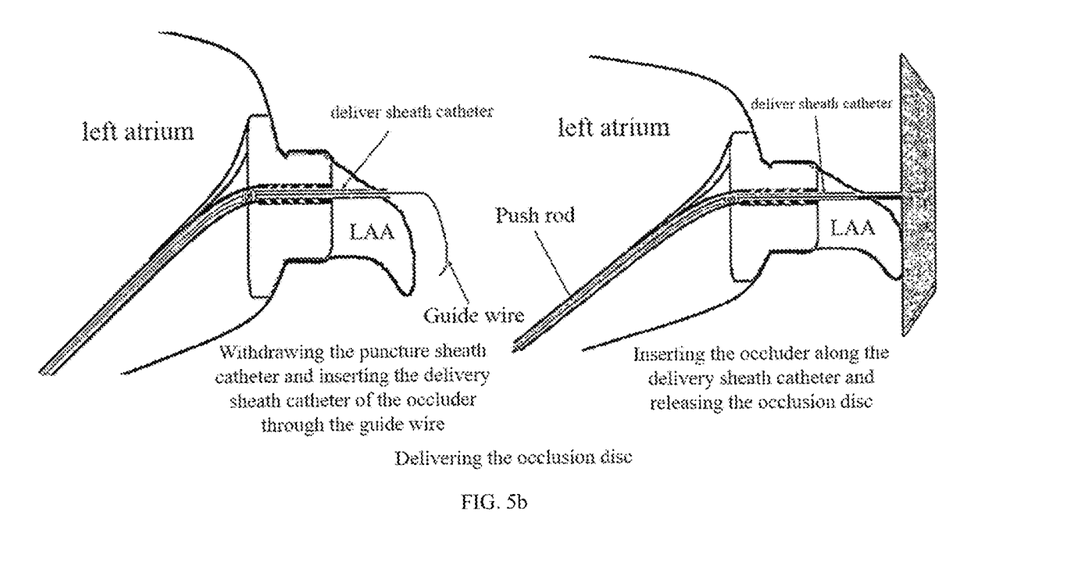
Figure 5C:
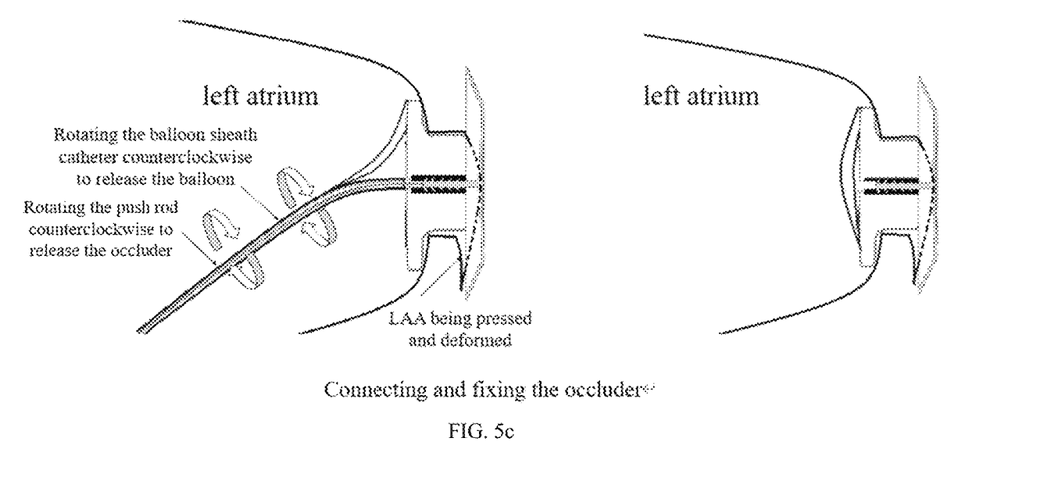
Figure 6A:
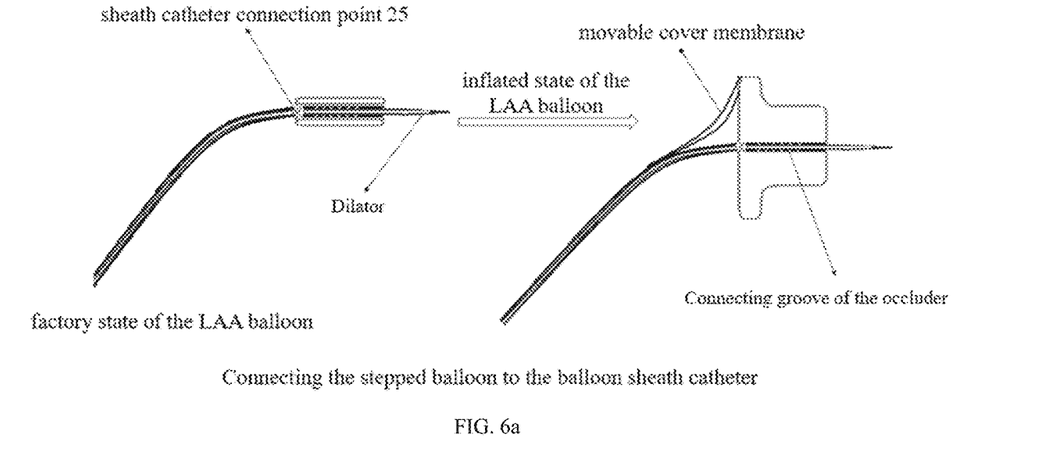
FIGS. 6*a*-6*e* show the balloon catheter of the left atrial appendage occluder according to the present disclosure.
Figure 6B:
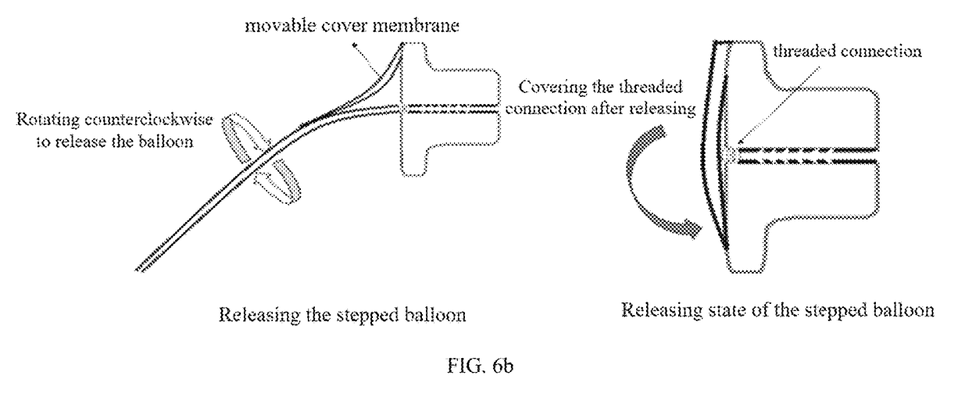
Figure 6C:
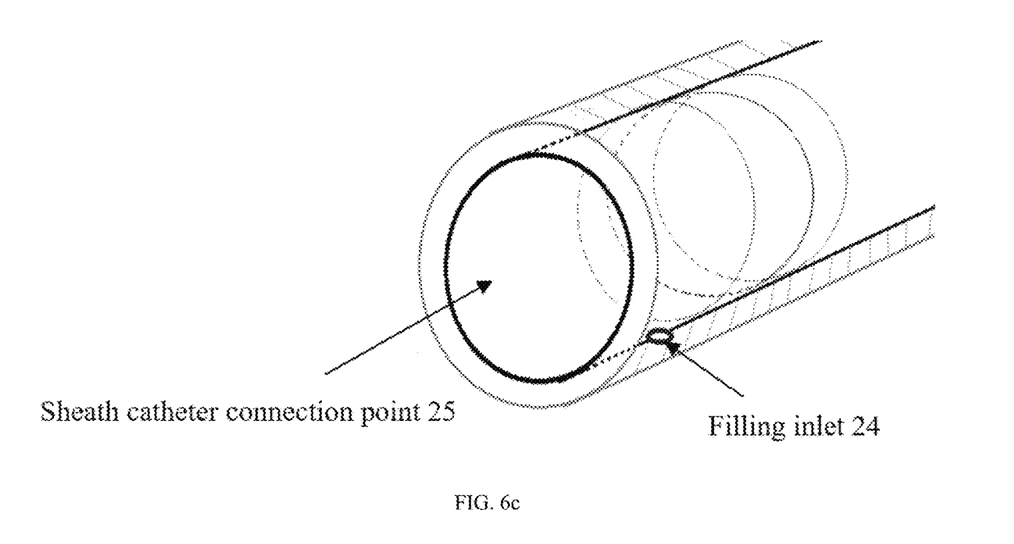
Figure 6D:
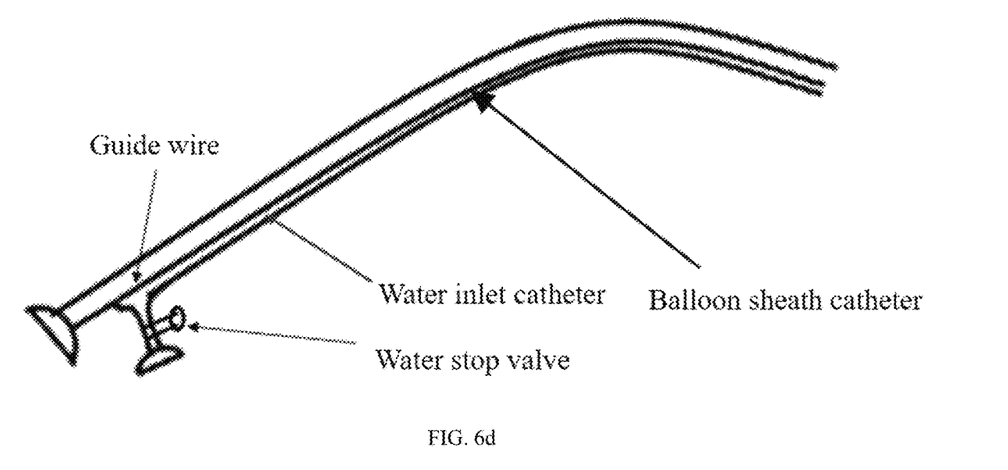
Figure 6E:
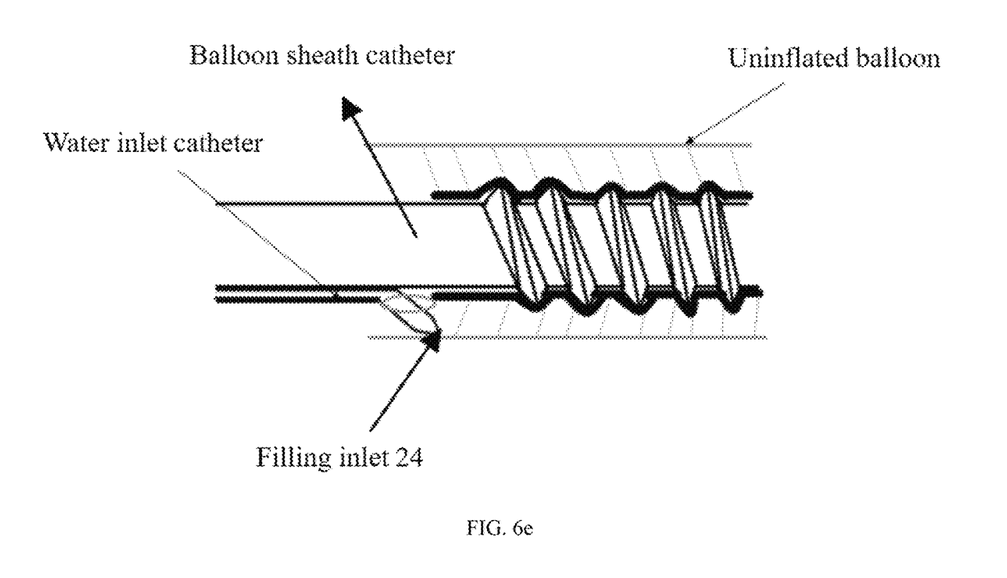

FIGS. 5a-5c show an implanting process of the left atrial appendage occlusion device according to the present disclosure. As shown in FIGS. 5a-5c, the implanting method includes the following steps:

Step 1, a catheter and a guide wire are conventionally delivered to the right atrium through a femoral vein; the guide wire is retained in the left atrium after puncturing the atrial septum; the balloon sheath catheter is connected to the stepped balloon by the sheath catheter connection point; the dilator is inserted into the balloon sheath catheter; the dilator and the balloon sheath catheter are delivered to the left atrium along the guide wire; the dilator is withdrawn; the pigtail catheter is delivered through the balloon sheath catheter; a direction of the catheter is adjusted; the pigtail catheter is delivered into the left atrial appendage; the balloon sheath catheter is delivered into the left atrial appendage along the pigtail catheter; and the stepped balloon is filled with a liquid through a water injection port at the distal end of the balloon sheath catheter; wherein the left atrial appendage orifice is completely occluded by the stepped balloon; the filling inlet connected to the balloon sheath catheter on the balloon is provided with a one-way valve; the balloon sheath catheter is provided with a hose; the hose is inserted into the one-way valve to inject water into and pump water from the balloon; the hose is pulled out after the left atrial appendage orifice is completely occluded; and the one-way valve on the balloon is automatically closed to prevent the liquid from leaking out.

Step 2, remaining blood in the left atrial appendage is pumped through the pigtail catheter, the pigtail catheter is withdrawn, and the occlusion device delivery sheath catheter is inserted along the balloon sheath catheter; wherein the delivery sheath catheter is provided with the dilator; the guide wire is inserted along the delivery sheath catheter to penetrate the left atrial appendage into the pericardial cavity with a high-frequency electrical energy; the occlusion device delivery sheath catheter is delivered along the guide wire to enter the pericardial cavity through the left atrial appendage; after the left atrial guide wire is exchanged to enter the pericardial cavity; the dilator and the guide wire are withdrawn; and the occlusion device delivery sheath catheter is retained in the pericardial cavity.

Step 3, the occlusion device is delivered along the occlusion device delivery sheath catheter after the occlusion disc is connected to the occlusion disc connecting steel cable; the canopy of the occlusion disc is released in the pericardial cavity; the delivery sheath catheter retracts; the left atrial appendage is pressed between the occlusion disc and the stepped balloon, the push rod and the balloon sheath catheter are fixed; the delivery sheath catheter continues to retract; and the connecting column of the occlusion disc is released inside the balloon sheath catheter; wherein the connecting column expands, the groove on the inner wall of the penetrating passage of the balloon is engaged with the annular protrusion on the outer periphery of the connecting column, and the occlusion disc can be released by rotating the connecting steel cable; the occlusion disc connecting steel cable and the occlusion device delivery sheath catheter are withdrawn, the balloon sheath catheter is disconnected from the stepped balloon, and the occlusion device is completely released; the movable cover membrane on the stepped balloon naturally disengages after the balloon sheath catheter is withdrawn; and the sheath catheter connection point and the penetrating passage are closed.

Preferably, in step 3, the hose is arranged in the water injection port at the distal end of the balloon sheath catheter; the head end of the hose is inserted into the one-way valve; water is injected into or pumped from the balloon through the hose before the balloon is separated from the sheath catheter; after the occlusion is completed and inspected, the hose is retracted at the water injection port at the distal end of the balloon sheath catheter; the hose is retracted into the sheath catheter, and the balloon sheath catheter is separated from the balloon by rotating the balloon sheath catheter.

In addition, before the occlusion disc is released by rotating the connecting steel cable, the occluder is inspected to determine whether the occlusion device can successfully occlude the left atrial appendage orifice by push and pull experiments, ultrasonic testing, an angiographic evaluation, and others. According to the need, the occluder can be withdrawn, the pressure can be increased, or the occluder can be replaced with another occluder. The occluder of the present disclosure can be withdrawn and released repeatedly. If the systematic positioning is not satisfactory, the balloon and the occlusion disc can be completely withdrawn to occlude again. After use, the size of the occlusion device can be replaced as required, which improves the utilization rate of the occlusion device and significantly improves the occlusion effect.

The above-mentioned embodiments are only intended to illustrate the implementation mode of the present disclosure and thus are described in detail, which cannot be construed as a limitation on the scope of protection of the present disclosure. It should be noted that, those having ordinary skill in the art can make various modifications and improvements without departing from the concept of the present disclosure, and these modifications and improvements shall fall within the scope of protection of the present disclosure. Therefore, the scope of protection of the present disclosure is defined by the appended claims.

What is claimed is:

1. A replaceable left atrial appendage occluder, comprising:
 a stepped balloon, and
 an occlusion disc;
 wherein
 the stepped balloon and the occlusion disc are connected and fixed to each other, and arranged on a left side and a right side of a left atrial appendage, respectively; and the left atrial appendage is pressed and occluded between the stepped balloon and the occlusion disc;
 the occlusion disc is an elastic umbrella-shaped mesh structure, and a barrier patch is arranged inside the occlusion disc;
 the stepped balloon comprises a hollow structure, and the stepped balloon after being filled forms a left atrial appendage orifice occlusion portion and a left atrial anchor portion; a diameter of the left atrial appendage orifice occlusion portion is larger than a left atrial appendage orifice; the left atrial appendage orifice occlusion portion is configured to completely fill and occlude the left atrial appendage orifice; a diameter of the left atrial anchor portion is larger than the diameter of the left atrial appendage orifice occlusion portion; the left atrial anchor portion is clamped on a left atrial wall of the left atrial appendage orifice to prevent the stepped balloon from sliding into the left atrial appendage; and
 a balloon filling inlet is arranged on a surface of the left atrial anchor portion, and the balloon filling inlet is configured to inject a liquid into the stepped balloon; a movable cover membrane is arranged on the surface of the left atrial anchor portion; and a surface of the stepped balloon is sealed after the movable cover membrane is closed; a penetrating passage is arranged in the stepped balloon; a side of the occlusion disc is provided with a connecting column, wherein the side of the occlusion disc contacts the left atrial appendage; the stepped balloon and the occlusion disc are fixed to each other by an extension connection of the penetrating passage and the connecting column.

2. The replaceable left atrial appendage occluder according to claim 1, wherein, a groove is arranged on an inner wall of the penetrating passage; an annular protrusion is arranged on an outer periphery of the connecting column; and the groove is engaged with the annular protrusion when the stepped balloon is connected to the occlusion disc.

3. The replaceable left atrial appendage occluder according to claim 2, wherein, the diameter of the left atrial appendage orifice occlusion portion is 2-8 mm larger than the left atrial appendage orifice; a diameter of a left side umbrella-shaped plate of the occlusion disc is 10-50 mm, and a diameter of the connecting column is 2-20 mm; and a length of the stepped balloon is 10-60 mm, the diameter of the left atrial appendage orifice occlusion portion is 10-90 mm, the diameter of the left atrial anchor portion is 20-100 mm, a thickness of the left atrial anchor portion is 4-20 mm, and the diameter of the left atrial anchor portion is 4-30 mm larger than the diameter of the left atrial appendage orifice occlusion portion.

4. The replaceable left atrial appendage occluder according to claim 3, wherein, the diameter of the left side umbrella-shaped plate of the occlusion disc is 30 mm, and the diameter of the connecting column is 8 mm; and the length of the stepped balloon is 20 mm, the diameter of the left atrial anchor portion is 10 mm larger than the diameter of the left atrial appendage orifice occlusion portion, and the thickness of the left atrial anchor portion is 6 mm.

5. The replaceable left atrial appendage occluder according to claim 1, wherein, a sheath catheter connection point is arranged at an end of the penetrating passage, wherein the end of the penetrating passage is close to a left atrium; and the sheath catheter connection point is a groove or a cannula.

6. The replaceable left atrial appendage occluder according to claim 5, wherein, the diameter of the left atrial appendage orifice occlusion portion is 2-8 mm larger than the left atrial appendage orifice; a diameter of a left side umbrella-shaped plate of the occlusion disc is 10-50 mm, and a diameter of the connecting column is 2-20 mm; and a length of the stepped balloon is 10-60 mm, the diameter of the left atrial appendage orifice occlusion portion is 10-90 mm, the diameter of the left atrial anchor portion is 20-100 mm, a thickness of the left atrial anchor portion is 4-20 mm, and the diameter of the left atrial anchor portion is 4-30 mm larger than the diameter of the left atrial appendage orifice occlusion portion.

7. The replaceable left atrial appendage occluder according to claim 6, wherein, the diameter of the left side umbrella-shaped plate of the occlusion disc is 30 mm, and the diameter of the connecting column is 8 mm; and the length of the stepped balloon is 20 mm, the diameter of the left atrial anchor portion is 10 mm larger than the diameter of the left atrial appendage orifice occlusion portion, and the thickness of the left atrial anchor portion is 6 mm.

8. The replaceable left atrial appendage occluder according to claim 1, wherein, the diameter of the left atrial appendage orifice occlusion portion is 2-8 mm larger than the left atrial appendage orifice; a diameter of a left side umbrella-shaped plate of the occlusion disc is 10-50 mm, and a diameter of the connecting column is 2-20 mm; and a length of the stepped balloon is 10-60 mm, the diameter of the left atrial appendage orifice occlusion portion is 10-90 mm, the diameter of the left atrial anchor portion is 20-100 mm, a thickness of the left atrial anchor portion is 4-20 mm, and the diameter of the left atrial anchor portion is 4-30 mm larger than the diameter of the left atrial appendage orifice occlusion portion.

9. The replaceable left atrial appendage occluder according to claim 8, wherein, the diameter of the left side umbrella-shaped plate of the occlusion disc is 30 mm, and the diameter of the connecting column is 8 mm; and the length of the stepped balloon is 20 mm, the diameter of the left atrial anchor portion is 10 mm larger than the diameter of the left atrial appendage orifice occlusion portion, and the thickness of the left atrial anchor portion is 6 mm.

10. The replaceable left atrial appendage occluder according to claim 1, wherein, a material of the stepped balloon is a polymer, rubber, or a polyester material, and the surface of the stepped balloon is coated with an anticoagulant coating.

* * * * *